United States Patent
Mueller et al.

(10) Patent No.: US 7,665,357 B2
(45) Date of Patent: Feb. 23, 2010

(54) ACCRETION ALARM FOR FIELD DEVICES

(75) Inventors: Alexander Mueller, Sasbach-Jechtingen (DE); Christoph Rompf, Greenwood, IN (US)

(73) Assignee: Endress + Hauser GmbH + Co. KG, Maulburg (DE)

( * ) Notice: Subject to any disclaimer, the term of this patent is extended or adjusted under 35 U.S.C. 154(b) by 421 days.

(21) Appl. No.: 10/562,224

(22) PCT Filed: Jun. 22, 2004

(86) PCT No.: PCT/EP2004/006707
§ 371 (c)(1),
(2), (4) Date: Dec. 23, 2005

(87) PCT Pub. No.: WO2005/001392
PCT Pub. Date: Jan. 6, 2005

(65) Prior Publication Data
US 2008/0072667 A1    Mar. 27, 2008

(30) Foreign Application Priority Data
Jun. 23, 2003    (DE) .............................. 103 28 296

(51) Int. Cl.
*G01F 23/28*    (2006.01)
(52) U.S. Cl. .................... 73/290 V; 73/54.01; 73/54.24
(58) Field of Classification Search ............... 73/290 R, 73/290 V; 340/612, 615, 617, 618, 620
See application file for complete search history.

(56) References Cited

U.S. PATENT DOCUMENTS

| | | | | |
|---|---|---|---|---|
| 4,383,443 A | * | 5/1983 | Langdon ................... 73/290 V |
| 4,594,584 A | | 6/1986 | Pfeiffer et al. | |
| 4,783,987 A | * | 11/1988 | Hager et al. ................ 73/32 A |
| 6,389,891 B1 | * | 5/2002 | D'Angelico et al. ...... 73/290 V |

FOREIGN PATENT DOCUMENTS

| | | |
|---|---|---|
| CH | 683 375 A | 2/1994 |
| DE | 42 01 360 | 7/1993 |
| DE | 44 05 238 | 8/1995 |
| DE | 100 14 724 A | 9/2001 |
| DE | 101 49 851 | 4/2003 |
| DE | 101 61 071 A | 6/2003 |
| DE | 101 61 072 | 6/2003 |
| DE | 101 62 043 | 6/2003 |
| DE | 103 23 063 | 12/2004 |
| WO | WO 02/42724 | 5/2002 |

* cited by examiner

*Primary Examiner*—Hezron Williams
*Assistant Examiner*—Mark Shabman
(74) *Attorney, Agent, or Firm*—Bacon & Thoms, PLLC

(57) ABSTRACT

A field device for monitoring and/or determining a process variable of a medium, wherein the process variable preferably is fill level, viscosity or density of the medium. The field device includes: an oscillatable unit; a driving/receiving unit, which excites the oscillatable unit to oscillate, or which receives the oscillations of the oscillatable unit, as the case may be; and a control/evaluation unit, which controls the oscillations of the oscillatable unit, or which evaluates the oscillations of the oscillatable unit, control/evaluation unit produces an accretion alarm, when the oscillation frequency (f) of the oscillations of the oscillatable unit falls below an adjustable limit value (G; $G_{Minimum}$; $G_{Maximum}$). The limit value (G; $G_{Minimum}$; $G_{Maximum}$) is determinable and/or calculable at least from measured and/or calculated dependencies of the oscillation frequency on process conditions and/or on the process variable to be monitored and/or determined.

4 Claims, 2 Drawing Sheets

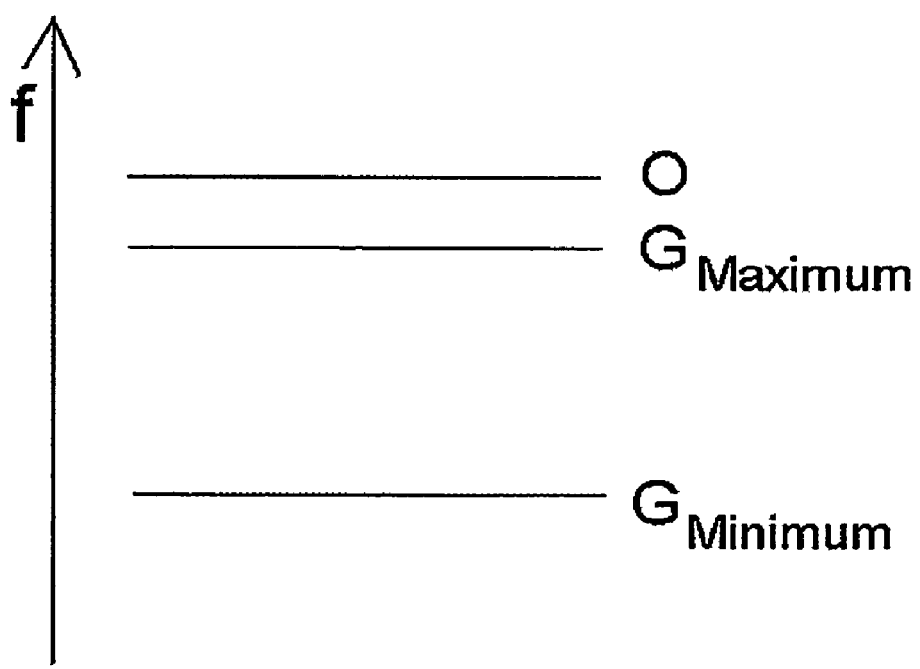

ACCRETION ALARM FOR FIELD DEVICES

FIELD OF THE INVENTION

The invention relates to a field device for monitoring and/or determining a process variable of a medium, wherein the process variable is preferably the fill level, viscosity or density of the medium. The field device includes: An oscillatable unit; a driving/receiving unit, which excites the oscillatable unit to oscillate, or receives the oscillations of the oscillatable unit, as the case may be; and a control/evaluation unit, which controls the oscillations of the oscillatable unit, or evaluates the oscillations of the oscillatable unit, also as the case may be. The medium is e.g. a liquid in a container.

BACKGROUND OF THE INVENTION

Field devices for measuring and/or monitoring the fill level of a medium in a container are produced and sold by the assignee under the mark "Liquiphant". Such a measuring device is usually composed of an oscillatable unit, a driving/receiving unit, and a control/regulating unit. The driving/receiving unit excites the oscillatable unit—most often, an oscillatable fork—to oscillate. The frequency (f) of oscillation depends e.g. on whether the oscillatable unit is oscillating in air or covered with medium. Thus, from the frequency, the degree of covering can be deduced. This can also be derived from the amplitude; usually, however, the frequency is evaluated. In the driving/receiving unit, a piezoelectric element is present, for example; this converts an electrical signal into a mechanical oscillation, which then is transferred via a suitable membrane, or diaphragm, to the oscillatable unit. Conversion of the mechanical oscillation into an electric signal occurs in the same way, in reverse. A feedback electronics, which amplifies and feeds the signal of the oscillatable unit back, and the electronics for evaluation and further processing of the oscillation, are combined in a control/evaluation unit. Such fill level measuring devices are usually applied as limit-level switches. In such case, the oscillatable unit is mounted at a determined position, e.g. inside the container, from which a fill level of the medium results. Measured can be either the subceeding, or falling beneath, of this fill height (protection against running empty, or minimum protection or minimum detection) or the exceeding of this fill height (protection against overfilling, maximum protection or detection). In the case of protection against running empty, the oscillatable unit first oscillates in the medium and then in air or e.g. in a second medium with a lesser density in the case of an interface detection (e.g. oil/water). The oscillation frequency in the case of oscillatable unit immersed in the medium, or in the medium with higher density, is less than in the case of oscillation in air or in the medium with the lesser density. Consequently, from the fact that the oscillation frequency becomes greater, or climbs above a certain threshold, it can be concluded that the oscillatable unit is oscillating freely, thus is no longer covered, or that the oscillatable unit is oscillating in the medium with the lesser density. This means that the medium with the higher density—this holds also for the case, from medium to air—has fallen below the fill level. On the basis of this information, for example, a drain can be closed, or an alarm can be triggered. Similar considerations hold for application as a maximum protection.

A problem concerns the formation of accretions. Some media, e.g. foaming liquids, coat the oscillatable unit and deposit on it. This accretion increases the mass of the oscillatable unit. Connected therewith is a lessening of the oscillation frequency (f), i.e., because of the additional mass, the oscillatable unit oscillates with a lesser frequency (f). If such a field device, whose oscillatable unit is coated with accretion, is used for protection against running empty, then there is the danger, that a "covered" report will be issued, even though the fork is actually oscillating freely, because the oscillation frequency (f) is, due to the accretion, clearly below the frequency evaluated as a measure for the fork being free. Safety is, consequently, no longer unconditionally assured; thus, recognizing the presence of accretion is very important. In the case in which the field device is used for protection against overfilling, recognizing accretion is likewise of interest, since the accretion leads also to a "covered" report, when the oscillatable unit is really oscillating freely. Thus, an accretion prevents reliable functioning of the field device.

SUMMARY OF THE INVENTION

Therefore, it is an object of the invention to monitor and/or measure a process variable of a medium, wherein an accretion leads to a corresponding alarm.

Such object of the invention is achieved by having the control/evaluation unit produce an accretion alarm, when the oscillation frequency (f) of the oscillations of the oscillatable unit falls below an adjustable limit value (G; $G_{Minimum}$; $G_{Maximum}$) wherein the limit value (G; $G_{Minimum}$; $G_{Maximum}$) is determinable and/or calculable at least from measured and/or calculated dependencies of the oscillation frequency (f) on process conditions and/or on the process variable to be monitored and/or to be determined. Accretion reduces the oscillation frequency (f). Therefore, it is checked, whether the frequency (f) lies below a limit value (G; $G_{Minimum}$; $G_{Maximum}$). In this case, an alarm, or an error signal, is issued. The limit value (G) is generally freely adjustable corresponding to the application and corresponding to the process conditions. In the case of $G_{Minimum}$ and $G_{Maximum}$, there are two distinct limit values for the application of the field device for fill level detection (this will be explained more in the following embodiments). The oscillation frequency (f) is not only dependent on accretion, but, rather, also on the process conditions—e.g. temperature, pressure, density, viscosity, etc.—and on the process variables, e.g. fill level. Oscillation frequency (f) is, moreover, among other things, dependent on the details of the oscillatable unit. These dependencies of frequency (f) on process conditions and process variable are measured e.g. in a calibration. The dependencies on process variable and process conditions are relative to, in each case, the details of the field device and, especially also, the details of the oscillatable unit. This calibration can then be placed e.g. in the field device itself or e.g. in a user manual. In this way, it is known, how frequency reacts to influences other than the process variable to be monitored and/or determined, and the appropriate limit value (G) can be set by measurement or calculation. The distinguishing between process condition and process variable depends, in such case, naturally, on what is being measured, so that, depending on application, a process condition can become a process variable, and vice versa. In the case of both, process variable and process condition, such thus involve physical and/or chemical variables, which influence the oscillation frequency. If the process variable is the fill level, then, for example, density, viscosity, temperature and pressure are the process conditions. If, however, density is the process variable, then fill level is a process condition. Since frequency also depends on temperature, this can also be a process variable. If accretion is to be recognized in the case of a field device used as a maximum switch, then the limit value ($G_{Maximum}$) must be set starting from the frequency which results, when the oscillatable unit is oscillating freely. In the case of use as a minimum switch, then, correspondingly, the frequency to be referenced is that which results when the oscillatable unit is covered. This relates, thus, to the process variable. If the field device is e.g. applied for viscosity monitoring, then a certain degree of covering—fill level is now a process condition—is required, which already leads to a lessening of the oscillation frequency.

In the determining or fixing of the limit value (G), it is always important to be sure that the limit value (G) is not so small, that a switching of the field device—e.g. at the freeing of the oscillatable unit in the case of use of the field device as a minimum switch—is no longer possible. Consequently, the dynamic of the oscillatable unit must always be considered. Under "dynamic" is meant, in this case, the frequency change resulting e.g. with the freeing of the oscillatable unit, e.g. the oscillatable fork. The dynamic, or frequency shift, of the oscillatable unit is usually independent of accretion, to the extent that the accretion does not have a greater mass than the oscillatable unit. Should e.g. the limit value G be 800 Hz compared to an oscillation frequency of 1000 Hz in air, and the oscillatable unit has a dynamic of 250 Hz, then the field device can report the transition from the covered state into the free state. If, however, the limit value G were set at 700 Hz, then the field device could not report the freeing in all cases, i.e., with reference to the dynamic, this limit value G is too small, or, that is to say, the difference between the limit value (G) and the frequency, above which the freeing is reported, is too great. A lifting of the limit value (G), in order to be consistent with the dynamic, is, in the case where the oscillatable unit is kept the same, then possibly associated with a limiting of the range of application, thus a limiting of the availability—e.g. with reference to a smaller range of density, temperature, or pressure. An advantage, however is the resulting greater safety as regards accretion. On the basis of these considerations, the application is already focussed on media, which tend toward accretion formation. Furthermore, a certain tolerance should be built in, so that small deviations and fluctuations do not lead too quickly to an alarm.

An embodiment provides that the process variable is fill level and that the limit value (G) is determinable and/or calculable as a function of the application of the field device, whether as a minimum switch ($G_{Minimum}$) or as a maximum switch ($G_{Maximum}$). The limit value (G) depends on whether the oscillatable unit is covered with the medium or whether it is oscillating freely, i.e. the limit value (G), therefore, also depends on the application of the field device. By the covering by the medium in the case of application as a minimum switch, the frequency is already clearly smaller. Consequently, this limit value ($G_{Minimum}$) is also smaller than the limit value ($G_{Maximum}$, which is needed in the case of application of the field device as a maximum switch. In the case of application as a maximum switch, it must, additionally, be assured that the limit value ($G_{Maximum}$) is also subceeded by the covering of the oscillatable unit by the medium. In the case of a discrete transition between uncovered and covered, this frequency jump caused by the dynamic of the oscillatable unit is clearly greater than that which should result from an accretion. However, if the transition occurs gradually, then the distinguishing between covered and accretion cannot be done directly. For this purpose of distinguishing between accretion and partial covering, a time constant is of interest, so that only after a long-lasting subceeding of the limit value ($G_{Maximum}$) is an alarm triggered. In the setting of such a time constant, however, then also the process conditions must be known. In the case of a maximum switch, one must thus distinguish between the subceeding of the limit value ($G_{Maximum}$), without that the corresponding, lower value—this can be, for example, the limit value ($G_{Minimum}$) for the application as a minimum switch—corresponding to the state in which the oscillatable unit is covered, be subceeded—this leads to an accretion alarm—and the subceeding of both frequency values, or the subceeding of the lower value, which results from the rising of the fill level—this leads to a "covered" report. If, for example, the oscillatable unit is an oscillatable fork and e.g. a solid material from the medium gets stuck between the tines of the fork, then it may not be possible to distinguish between accretion and the medium, i.e. at a subceeding of the maximum fill level, the field device still is issuing a covered report. Such a sticking can, however, usually also only be cleared by e.g. a manual intervention, i.e. for such extreme cases, a plausibility review of the report issued by the field device is still necessary. According to the invention, this problem is overcome through the recognition that, in the case of such a sticking of the fork, the received amplitude is minimized in such a manner that the exciting electronics of the field device jumps to an eigenresonance, which usually lies below a limit value (G) for an accretion alarm. The availability is, as required, reduced in favor of the increased functional safety.

An embodiment provides that the limit value (G; $G_{Minimum}$; $G_{Maximum}$) is determinable and/or calculable from the smallest oscillation frequency (f) as a function of the corresponding maximum (with reference to the field device) allowable process conditions and/or as a function of the maximum (with reference to the field device and/or with reference to the application) allowable process variable to be monitored and/or determined. For the field device, the range of application is generally limited with reference to some process conditions. In this way, it is prevented that a destruction of the entire field device, or of individual components of the field device, can occur. However, even before destruction, it is not always assured that there will not be some downtime. Consequently, usually certain limitations exist. For example, temperature is limited, in order that the electronics not be damaged by heat or in order that, for example, adhesive not become liquid again. Associated with the limits of application are usually also the greatest changes of oscillation frequency (f). For example, the frequency at the greatest allowable pressure is smaller than the frequency at the smallest allowed pressure. Consequently, the limit value (G; $G_{Minimum}$; $G_{Maximum}$) is to be determined from the frequency at maximum pressure. A grater pressure would, it is true, reduce the frequency further, but the field device is not qualified for a higher pressure. From a combination of the maximum allowable process conditions, the smallest oscillation frequency (f) can, therefore, be determined, and, therewith, the corresponding limit value (G). In terms of further parameters, there is still the process variable to be measured, e.g. that the oscillatable unit is covered. Thus, as a function of the application, also the process variable is to be considered.

An embodiment provides that the limit value (G; $G_{Minimum}$; $G_{Maximum}$) is determinable and/or calculable taking into consideration a maximum allowable accretion, or taking into consideration a frequency change associated with the maximum allowable accretion. A certain, very small accretion can be quite permissible, because the sensors are built with sufficient quality, such that a small accretion only disturbs the measurement negligibly. Furthermore, it is not practical to forbid even the slightest accretion, since that would be scarcely possible under real conditions. For that, a medium would be required that never produces any accretion, and, in such case, an accretion alarm would not be necessary. The maximum allowable accretion is to be set e.g. on the basis of the type of medium and type of application.

An embodiment includes that the process conditions involve temperature and/or pressure and/or density and/or viscosity and/or fill level of the medium. For temperature and pressure, there is, in each case, a maximum allowable region, beyond which the field device is damaged or can no longer function reliably. Density and viscosity of the medium are variables, which likewise have an influence on the oscillation frequency (f). In many applications, the process variable is fill level. Should, however, it be, for example, density which is to be monitored, then fill level must be known accurately (e.g. complete covering).

An advantageous embodiment provides that a review unit is provided, which produces an accretion alarm independently of the control/evaluation unit, when the oscillation frequency (f) of the oscillations of the oscillatable unit subceeds, or falls below, an adjustable limit value (G; $G_{Minimum}$; $G_{Maximum}$). Such an independent review unit has the advantage that the functionality of the field device is watched redundantly. This is relevant e.g. for applications having increased requirements for the functional safety of electric, electronic or programmable, electronic systems. The review unit can, in such case, be arranged spatially separated from the control/evaluation unit; it can, however, also be a component of the control/evaluation unit.

An embodiment provides that the control/evaluation unit produces a "free" report, when the oscillation frequency of the oscillations of the oscillatable unit exceed an adjustable, over-, or upper-, value (O), wherein the over-value (O) is determinable and/or calculable from measured and/or calculated dependencies of the oscillation frequency (f) on process conditions and/or on the process variable to be determined and/or monitored. The oscillatable unit is, thus, first in a covered state. If the medium falls below the predetermined fill level, then the unit is oscillating freely—or, as discussed above, in a medium with a lesser density—and, at the same time, with a higher oscillation frequency (f). Depending on the type of oscillatable unit and on the type of installation, the frequency (f) can, under the right circumstances, change gradually. Most often, however, a signal is only issued, when the oscillatable unit is oscillating completely freely. Therefore, the transition to a higher frequency alone is still no criterion. Consequently, an over-value (O) is of interest, whose exceeding is equal to a completely free, oscillatable unit. As in the case of the limit value (G; $G_{Minimum}$; $G_{Maximum}$), the dependencies of the oscillation frequency (f) on the process conditions and/or the process variable are measured or calculated. From a practical point of view, the values for determining the limit value (G; $G_{Minimum}$; $G_{Maximum}$) can, in such case, be made use of, since the same oscillatable unit and, consequently, the same dependencies, are involved. The frequency range between the over-value (O) and the limit value in the case of application as maximum protection ($G_{Maximum}$) results, consequently, from the oscillations of the oscillatable unit without covering or in the medium of lesser density and is determined by the dependencies of the oscillation on the process conditions. This over-value (O) for reporting of the freely oscillating fork is also relevant for the determining and/or monitoring of such process variables as density and viscosity.

An embodiment includes that the over-value (O) is determinable and/or calculable from the greatest oscillation frequency (f) as a function of the corresponding maximum (with reference to the field device) allowable process conditions and as a function of the fact that the oscillatable unit is oscillating in the uncovered state. If it was still important in the case of the limit value (G; $G_{Minimum}$) that the oscillatable unit was covered, then it must here, in keeping with the definition of the over-value (O), oscillate freely. The over-value (O) is, consequently, to be determined e.g. from the frequency at minimum pressure, since that is where, in such case, the greatest frequency results.

An embodiment provides that the over-value (O) is determinable and/or calculable taking into consideration a maximum allowable accretion, or a frequency change associated with the maximum allowable accretion. Also, here, a minimum amount of accretion should be permissible. Furthermore, also a certain tolerance should be built-in with reference to the over-value (O), so that e.g. already a single air bubble does not produce the "free" report.

In the case of the limit value (G; $G_{Minimum}$) and in the case of the over-value (O), attention should be paid that the difference between the two values is greater than the dynamic of the oscillatable unit, so that an oscillation only slightly above the limit value (G), e.g. in the case of covered oscillatable unit, can still show a freeing, when such happens. The limit value in the case of use as a maximum switch, $G_{Maximum}$, is not affected by this, since this limit value $G_{Maximum}$ relates to the uncovered, oscillatable unit and since the difference between the limit value $G_{Maximum}$ and the over-value O is given by the different effects of the process variables. An opportunity of the implementation is that limit value (G) and over-value (O) are each individually set on the basis of the density or viscosity of the medium. Thus, a choice is to be made between a general limitation, e.g. with reference to the allowable density, or a special tuning for the medium and process conditions possible in the process, such as e.g. the occurring temperatures.

BRIEF DESCRIPTION OF THE DRAWINGS

The invention will now be explained in greater detail on the basis of the drawings, the figures of which show as follows:

FIG. 2 a not-to-scale, schematic presentation of individual frequencies.

DESCRIPTION OF THE PREFERRED EMBODIMENT

Figure 1:
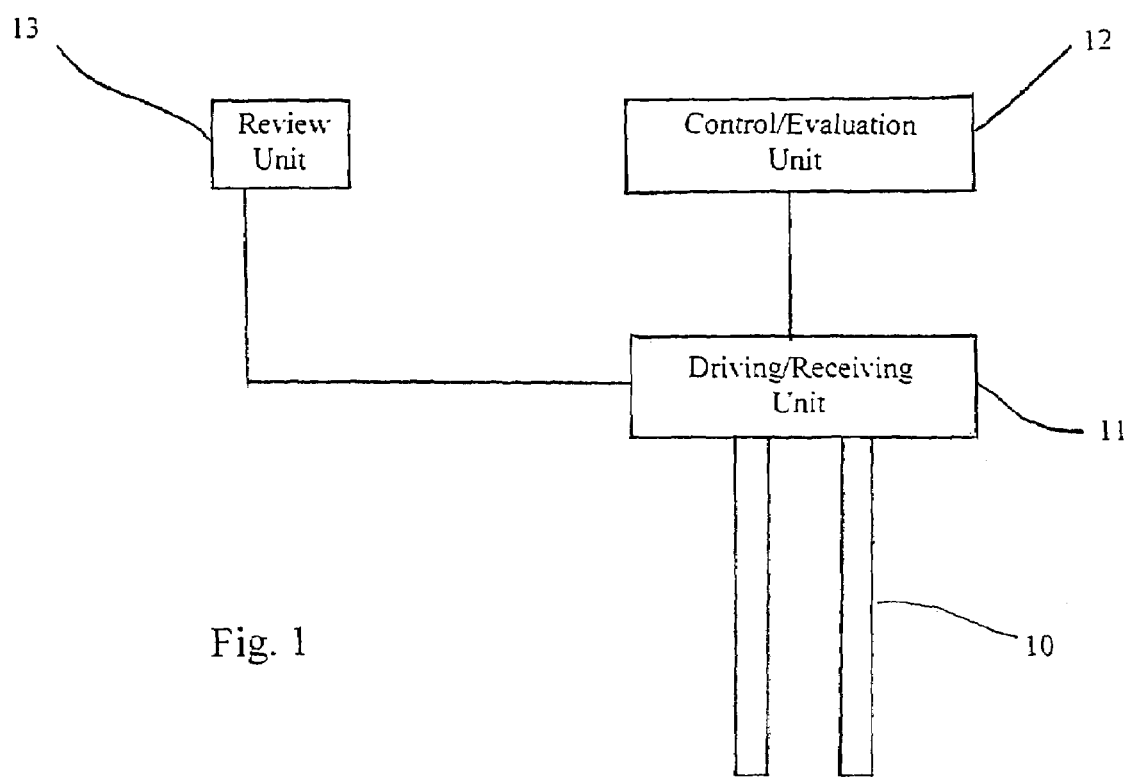
FIG. 1 a block diagram of the apparatus.

FIG. 1 shows the field device 1 composed of the oscillatable unit 10—here an oscillatable fork—the driving/receiving unit 11 and the control/evaluation unit 12. Such a field device 1 is placed, for example, near the floor of a container, in which the medium to be monitored is located. If the medium subceeds, or falls beneath, this fill level, then the oscillatable unit oscillates in air and has, therefore, a higher oscillation frequency f (minimum protection). This is processed by the control/evaluation unit 12 into a signal. Because of an accretion, however, the oscillation frequency f could already be so much reduced, that even the freed oscillatable fork oscillates below the threshold recognized by the control/evaluation unit 12 as freely oscillating. Consequently, no alarm is triggered, and a pump could, for example, run hot, a condition which is dangerous in the case of flammable media. To handle this, there is provided in the illustrated example a review unit 13, which checks, whether the oscillation frequency f falls below the limit value G. This additional monitoring can e.g. trigger an alarm independently of the control/evaluation unit 12. This is important e.g. for applications having increased need for functional safety. The review unit 13 can, however, also be part of the control/evaluation unit 12.

In FIG. 2, the individual frequencies, or limit values, are drawn schematically and not-to-scale. Frequency increases from below upwards. Below is the limit value $G_{Minimum}$ for application as a minimum switch or for protection against running empty. This limit value $G_{Minimum}$ is also subceeded, or fallen beneath, when e.g. the oscillatable fork becomes stuck and the electronics of the field device jumps to the eigenresonance of the fork. Above $G_{Minimum}$ lies the limit value $G_{Maximum}$, which is used in the case of application as a maximum switch, or for overflow protection. This limit value $G_{Maximum}$ is greater than the limit value $G_{Minimum}$, since the oscillation frequency experiences a very strong reduction by immersion into the medium, which means reciprocally that an accretion on the field device being used as a maximum switch would have to be very large, in order to subceed this lower limit value $G_{Minimum}$. Formulated generally, the limit value G depends on which process conditions are prevailing and what is to be measured. Farther up is the over-value O, whose exceeding leads to the report that the mechanically oscillatable unit is oscillating freely or in a medium of lesser density. Above the over-value O, yet another value can be provided, whose exceeding leads to a corrosion alarm. Between $G_{Minimum}$ and $G_{Maximum}$ is a zone with frequencies, which can occur only when accretion is on the mechanically oscillatable unit or when process conditions lie outside the design specifications of the field device, since the limit values $G_{Minimum}$ and $G_{Maximum}$ already contain the frequency dependencies for the process conditions.

The invention claimed is:

1. A field device for monitoring and/or determining a process variable of a medium, wherein the process variable is a fill level, viscosity or density of the medium, comprising:
   an oscillatable unit;
   a driving/receiving unit, which excites said oscillatable unit to oscillate, or which receives oscillations of said oscillatable unit; and
   a control/evaluation unit, which controls the oscillations of said oscillatable unit, or which evaluates the oscillations of said oscillatable unit wherein:
   said control/evaluation unit produces an accretion alarm, when the oscillation frequency of the oscillations of said oscillatable unit falls below an adjustable limit value;
   said adjustable limit value is determined and/or calculated from the smallest oscillation frequency as a function of the corresponding maximum (with reference to the field device) allowable process conditions and/or as a function of the maximum (with reference to the field device and with reference to the application) allowable process variable to be monitored and/or determined;
   said process conditions involve temperature and/or pressure and/or density and/or viscosity and/or fill level of the medium;
   the process variable is fill level;
   said adjustable limit value is determined and/or calculated as a function of the use of the field device, whether as a minimum switch or as a maximum switch;
   said control/evaluation unit produces a report, when the oscillation frequency of the oscillations of said oscillatable unit exceed an adjustable over-value;
   said adjustable over-value is determined and/or calculated from measured and/or calculated dependencies of the oscillation frequency on the process variable to be determined and/or to be monitored; and
   said adjustable over-value is determined and/or calculated from a greatest oscillation frequency as a function of corresponding maximum, in reference to the field device, allowable process conditions and as a function of said oscillatable unit oscillating uncovered.

2. The field device as claimed in claim 1, wherein:
   said adjustable limit value is determined and/or calculated taking into consideration a frequency change associated with a maximum allowable accretion.

3. The field device as claimed in claim 1, further comprising:
   a review unit which produces an accretion alarm independently of said control/evaluation unit, when the oscillation frequency of said oscillations of said oscillatable unit falls below an adjustable limit value.

4. The field device as claimed in claim 1, wherein:
   said adjustable over-value is determined and/or calculated taking into consideration a maximum allowable accretion, or a frequency change associated with the maximum allowable accretion.

\* \* \* \* \*

UNITED STATES PATENT AND TRADEMARK OFFICE
CERTIFICATE OF CORRECTION

PATENT NO.        : 7,665,357 B2                               Page 1 of 1
APPLICATION NO. : 10/562224
DATED             : February 23, 2010
INVENTOR(S)       : Mueller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Fourth Day of January, 2011

David J. Kappos
*Director of the United States Patent and Trademark Office*